(12) United States Patent
Dicks et al.

(10) Patent No.: US 7,364,356 B2
(45) Date of Patent: Apr. 29, 2008

(54) METHOD AND DEVICE FOR THE CONTACTLESS DETERMINATION OF THE BODY TEMPERATURE

(75) Inventors: Bernd-Michael Dicks, Luebeck (DE); Jochim Koch, Ratzeburg (DE)

(73) Assignee: Dräger Medical AG & Co. KG, Lübeck (DE)

( * ) Notice: Subject to any disclaimer, the term of this patent is extended or adjusted under 35 U.S.C. 154(b) by 0 days.

(21) Appl. No.: 11/470,047

(22) Filed: Sep. 5, 2006

(65) Prior Publication Data
US 2007/0086506 A1    Apr. 19, 2007

(30) Foreign Application Priority Data
Oct. 18, 2005    (DE) .................. 10 2005 049 676

(51) Int. Cl.
*G01J 5/00* (2006.01)
*A61B 5/01* (2006.01)

(52) U.S. Cl. .................. 374/121; 600/549; 600/474

(58) Field of Classification Search ............... 374/121; 600/474, 549
See application file for complete search history.

(56) References Cited

U.S. PATENT DOCUMENTS 6,000,845 A * 12/1999 Tymkewicz et al. ......... 374/155

2003/0142723 A1 * 7/2003 Laurence et al. ........... 374/121
2005/0271117 A1   12/2005 Grassl et al.
2006/0233216 A1 * 10/2006 Schuele .................... 374/130

FOREIGN PATENT DOCUMENTS

| DE | 19842403 | 3/2000 |
| DE | 102004027443 | 7/2005 |
| DE | 102004027443 B3 | 7/2005 |
| WO | WO 02/103306 | 12/2002 |

* cited by examiner

*Primary Examiner*—Gail Verbitsky
*Assistant Examiner*—Megann E Vaughn
(74) *Attorney, Agent, or Firm*—McGlew and Tuttle P.C.

(57) ABSTRACT

A method is provided for the contactless determination of the body core temperature of a person (7), wherein the surface temperature of the person (7) is detected at a measuring site (6) on the body by means of a temperature sensor unit (2) arranged at a spaced location therefrom. The sensor signal generated by the temperature sensor unit (2) is sent to an evaluating unit (3) for evaluating the sensor signal and for calculating the body core temperature, and the temperature signal generated in the evaluating unit (3) is sent to a display unit (4) for the optical display of the body core temperature determined. The temperature sensor unit (2) locally identifies a measuring area (8) on the body in a first step and the measuring area (8) on the body is resolved by the temperature sensor unit (2) in a second step such that the measuring site (6) on the body is detected and the detection is carried out by the temperature sensor unit (2) at this measuring site (6) on the body.

16 Claims, 3 Drawing Sheets

METHOD AND DEVICE FOR THE CONTACTLESS DETERMINATION OF THE BODY TEMPERATURE

CROSS REFERENCE TO RELATED APPLICATIONS

This application claims the benefit of priority under 35 U.S.C. § 119 of German Patent Application DE 10 2005 049 676.8 filed Oct. 18, 2005, the entire contents of which are incorporated herein by reference.

FIELD OF THE INVENTION

The present invention pertains to a method for the contactless determination of the body core temperature of a person, wherein the surface temperature of the person is detected at a measuring site on the body by means of a temperature sensor unit arranged at a spaced location therefrom, the sensor signal generated by the temperature sensor unit is sent to an evaluating unit for evaluation of the sensor signal and for calculating the body core temperature, and the temperature signal generated in the evaluating unit is sent to a display unit for the optical display of the body core temperature determined.

Furthermore, the present invention pertains to a measuring device for the contactless determination of the body core temperature of a person with a temperature sensor unit for detecting a surface temperature of the person's body, with an evaluating unit for evaluating the sensor signal sent by the temperature sensor unit as well as for calculating a temperature signal, and with a display unit for the visual and/or acoustic display of the body core temperature of the person.

BACKGROUND OF THE INVENTION

A measuring device for the contactless determination of the body temperature of a person, which comprises, on the one hand, a temperature sensor unit for the detection of a surface temperature of the person's body, is known from DE 10 2004 027 443 B3. On the other hand, the prior-art measuring device comprises an evaluating unit for evaluating the sensor signal detected by the temperature sensor unit and for calculating a current temperature signal, which is then visually reproduced in a downstream display unit. To enable a measurement to take place, it is necessary to accurately align the prior-art measuring device with the desired site of measurement on the body. Should the measuring device be aligned, for example, with cooler regions of the body or with the clothing of the person, undesired mismeasurements would occur. Furthermore, mismeasurements would also occur in case of incorrect alignment when the temperature sensor unit detects the temperature of heated respiration tubes, heated infusion tubes or parts of thermotherapy devices.

SUMMARY OF THE INVENTION

The object of the present invention is therefore to provide a method for the contactless determination of the body temperature of a person as well as a measuring device such that accurate, reliable and contactless determination of the body core temperature of the person is made possible with a low operating effort.

To accomplish this object, the method according to the present invention provides that the temperature sensor unit locally identifies a measured area on the body in a first step and that the measured area on the body is resolved by the temperature sensor unit in a second step such that the measuring site on the body is detected and the detection is carried out by the temperature sensor unit at this measuring site on the body.

The special advantage of the method according to the present invention is that accurate determination of the body core temperature is always made possible by the automatic scanning of a measured area on the body. On the one hand, it is sufficient for the temperature sensor unit to be aligned with the body or a measured area on the body at the beginning of the measurement. This can be carried out manually or automatically. The temperature sensor unit is then accurately aligned with a preset measuring site on the body, at which the detection of the surface temperature is carried out, by scanning the measured area on the body or by resolution by sensors arranged in a line or in a two-dimensional arrangement. Manual alignment of the temperature sensor unit with the measuring site on the body is therefore no longer necessary. On the other hand, continuous, automatic alignment of the temperature sensor unit is performed for the case in which the body, especially of an infant in an incubator, is moving and changes its position. The temperature sensor unit quasi "follows" the measuring site on the body due to the continuous scanning and resolution of the measuring area on the body, so that the temperature sensor unit is always adjusted to the preset measuring site on the body.

Due to the fact that the scanning and the resolution is limited to the measuring area on the body, temperature measurement can take place with high resolution and with a narrow range of variation. The resolution of a scanning motion that otherwise takes place over the entire body would be lower.

According to a variant of the method according to the present invention, the scanning of the measuring area on the body can take place continuously or at preset, fixed or variable time intervals. Thus, continuous or quasi-continuous detection of the surface temperature of a patient can be carried out for determination of temperature over a longer period of time in an especially well-tempered area on the body.

According to a variant of the present invention, the temperature sensor unit can be aligned with a measuring area on the body manually or automatically by a scanning unit provided for this purpose. A relatively coarse alignment of the temperature sensor unit with the body can thus be performed at the beginning of the measuring operation in a user-friendly manner.

To accomplish the object, the present invention provides a scanning unit associated with the temperature sensor unit such that the temperature sensor unit is automatically aligned with the measuring site on the body.

The special advantage of the measuring device according to the present invention is that by providing an additional scanning unit, adaptation of the position of the temperature sensor unit in relation to a measuring site on the body is made possible in a user-friendly manner. The scanning unit makes possible the scanning of the body in such a way that the measurement takes place at a measuring site on the body at which the surface temperature is high relative to the surface temperatures of adjacent areas. Thus, the temperature measurement can be carried out, for example, by detecting the surface temperature in the area of the ear or in the area of the eye. Due to the fact that quasi a "readjustment" of the temperature sensor unit is performed, a relatively accurate temperature measurement is guaranteed in a user-friendly manner.

According to a variant of the measuring device, the temperature sensor unit may have one or more infrared sensors, which are designed as spot sensors and/or as sensors arranged in a row or in a matrix-like pattern. Thus, area-covering scanning and resolution of the site of the measured value can take place in connection with a one-dimensional or two-dimensional sensor carrier.

According to a variant of the present invention, the scanning unit has an actuator or a joint, which acts directly on the sensor carrier carrying the temperature sensor unit and makes possible a relatively precise path of motion of the sensors of the temperature sensor unit. For example, the actuator may be designed as a stepping motor.

According to a variant of the present invention, a temperature stabilizing means is provided, so that there always is a significant difference between the surface temperature of the skin to be measured and the ambient temperature.

According to a variant of the present invention, an orientation field is detachably placed in a measuring area on the body or on a measuring site on the body, so that there is a reference point for the temperature sensor unit, from which point controlled alignment in the direction of the measuring site can be initiated by means of the scanning unit. The orientation field offers the possibility of optically identifying a fixed site on the body. The identification can be recognized, for example, by a web camera.

According to a variant of the present invention, the body or a thermotherapy apparatus, for example, an incubator, may be provided with a calibration field, which has a defined emissivity and/or a preset temperature. By aligning the temperature sensor unit with the calibration field, calibration of the temperature measurement is possible, as a consequence of which the absolute accuracy of temperature measurement increases. This calibration field can be found regularly or as needed. The calibration may be initiated after a plausibility check of the measured values. The temperature of the calibration field is preferably measured by the temperature regulation of a thermotherapy apparatus, at which the measuring device is arranged. As an alternative, the temperature measurement may, however, also be taken independently from the thermotherapy apparatus.

An exemplary embodiment of the present invention will be explained below on the basis of a drawing. The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

DESCRIPTION OF THE PREFERRED EMBODIMENTS

Figure 1:
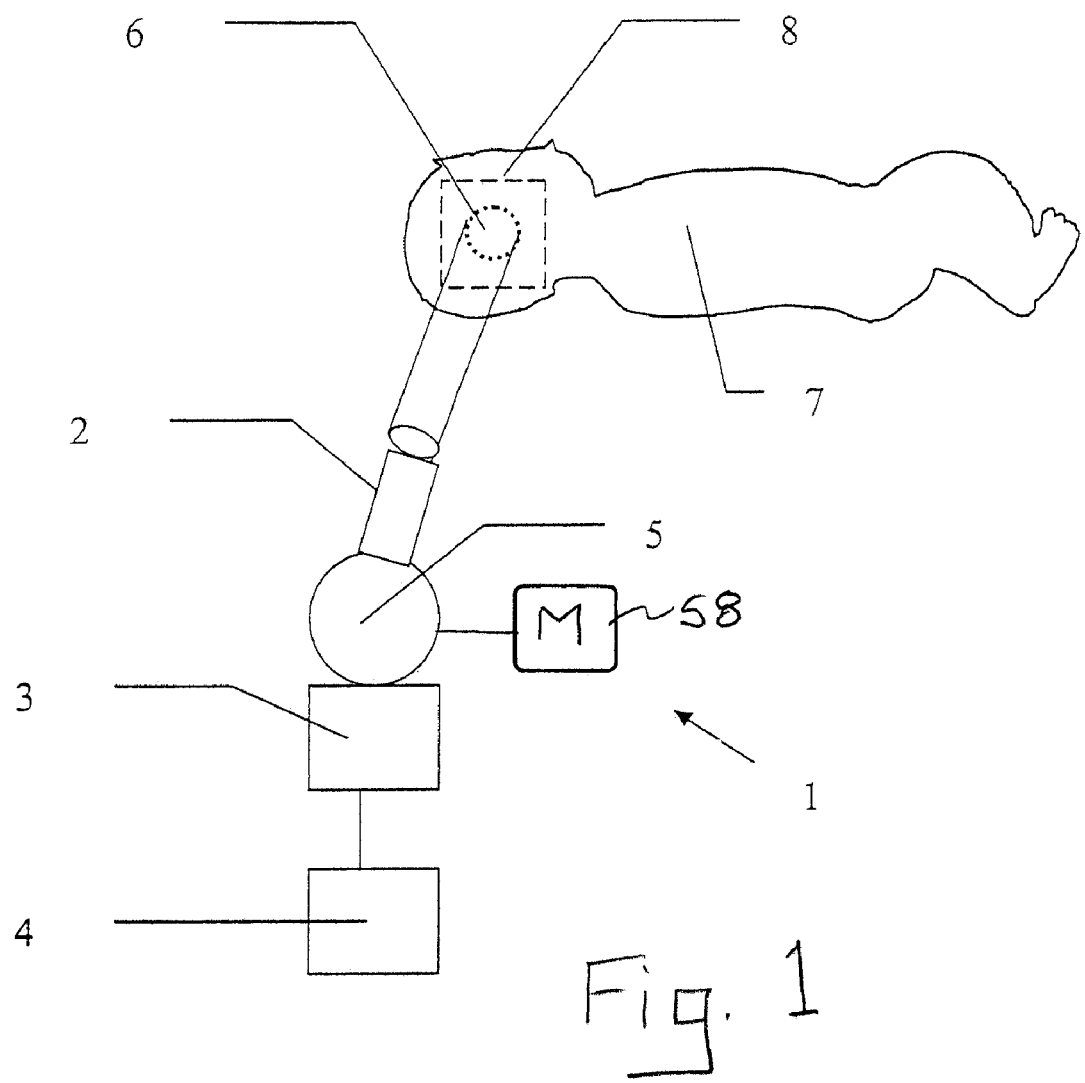
FIG. 1 is a block diagram of a measuring device for the contactless determination of the body core temperature.

Referring to the drawings in particular, a measuring device 1 according to the present invention for the contactless determination of the body temperature of a person has essentially a temperature sensor unit 2 for the detection of a surface temperature (skin temperature $T_{h1}$), an evaluating unit 3 for evaluating the sensor signal detected by the temperature sensor unit 2 and for calculating a core temperature value $T_c$, a display unit 4 for the visual and/or acoustic display of the body core temperature $T_c$, and a scanning unit 5, by means of which the temperature sensor unit 2 is automatically aligned with a measuring site 6 on the body.

The measuring site 6 on the body may be, for example, the area of an ear of an infant 7, who is lying in an incubator. To measure the body core temperature $T_c$, an operator can align the temperature sensor unit 2 with a measuring area 8 on the body, which encompasses the measuring site 6 on the body. The measuring area 8 on the body may be formed, for example, by the head of the infant 7. As an alternative, it is also possible that the operator aligns the temperature sensor unit 2 or the measuring device 1 with any desired area on the body of the infant 7. As an alternative, the alignment of the temperature sensor unit 2 with the measuring area 8 on the body may also be performed by the scanning unit 5 itself.

In a next, second step, the scanning unit 5 makes possible the scanning of the measuring area 8 on the body while continuously detecting the skin temperature $T_{h1}$ until the alignment of the temperature sensor unit 2 with the measuring site 6 on the body is reached. The measuring site 6 on the body is characterized in that an especially high skin temperature $T_{h1}$ can be measured at it, so that, on the whole, more accurate determination of the body core temperature $T_c$ is ensured. The measuring site 6 on the body may also be arranged, as an alternative to the area of the ear, in the temporal area, at the eye or on the abdomen. The measured signals, which were determined by detection at the measuring site 6 on the body, are then used for the measurement.

Figure 2:
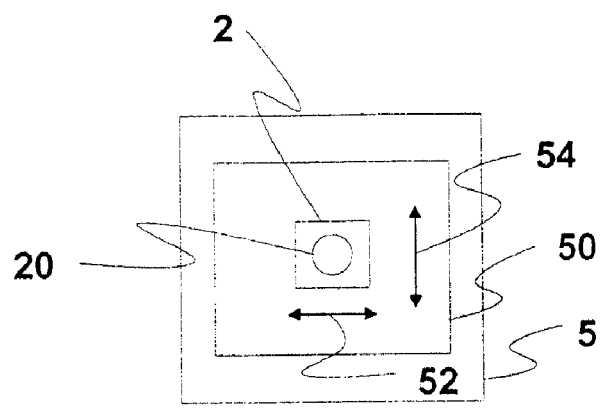
FIG. 2 is a schematic view of a temperature sensor unit and sensor carrier of the scanning unit.

The temperature sensor unit 2 may have one or more infrared sensors 20 as shown in FIG. 2. The infrared sensors 20 detect the skin temperature $T_{h1}$ in a contactless manner. For example, the temperature sensor unit 2 may have a spot sensor 20, which scans the area of the measuring site 6 on the body or of the measuring area 8 on the body in conjunction with a two-dimensionally movable sensor carrier 50 of the scanning unit 5.

Figure 3A:
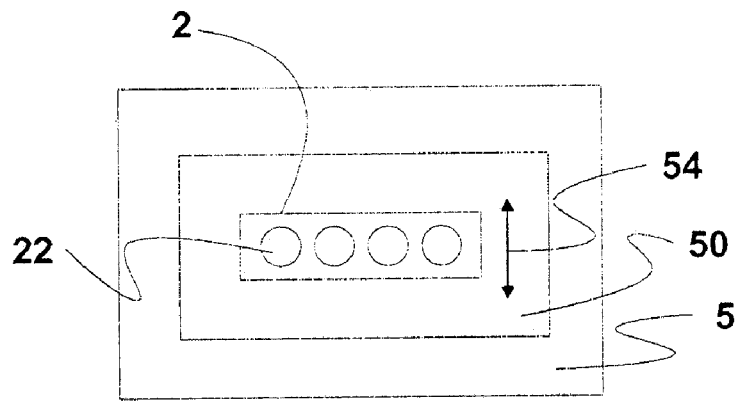
FIG. 3a is a schematic view of another temperature sensor unit and sensor carrier of the scanning unit.
Figure 4:
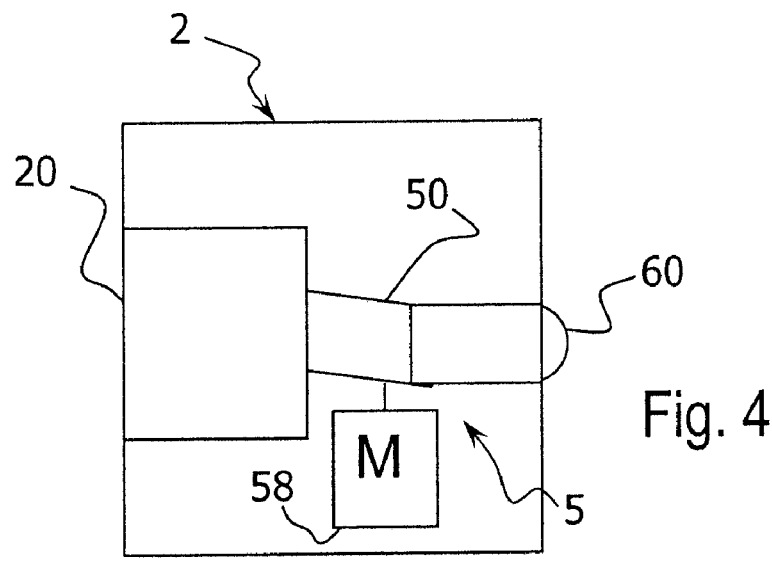
FIG. 4 is a schematic view of a temperature sensor unit housing with sensor carrier and scanning unit, sensor and optical system.
Figure 5:
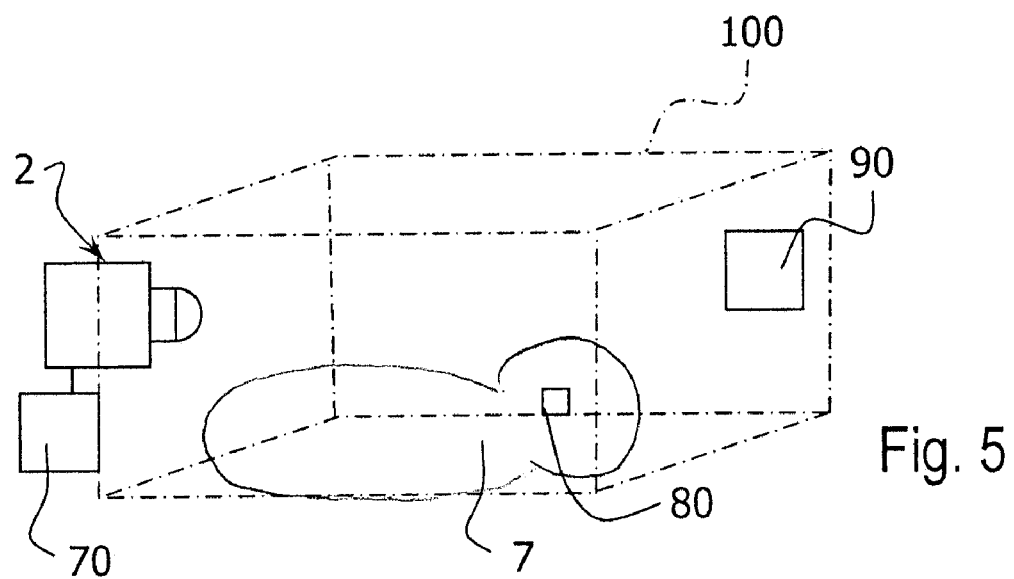
FIG. 5 is a schematic view showing an incubator in dot-dash line and showing a temperature sensor unit housing with sensor carrier and scanning unit, sensor and optical system and accessories for body temperature determination.

According to an alternative embodiment, the temperature sensor unit 2 may also have a number of infrared sensors 22 arranged in a line as shown in FIG. 4. The temperature sensor unit 2 scans the area of the measuring site 6 on the body or of the measuring area 8 on the body in conjunction with a one-dimensionally movable sensor carrier 50 of the scanning unit 5, as shown in FIG. 3a.

Figure 3B:
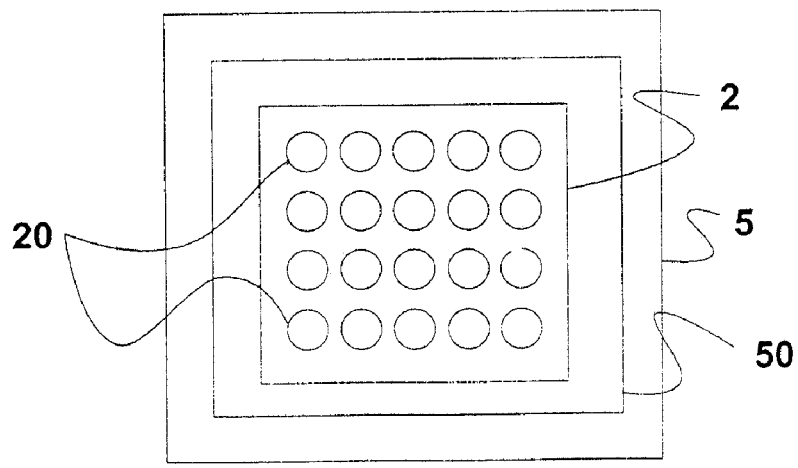
FIG. 3b is a schematic view of another temperature sensor unit and sensor carrier of the scanning unit.

According to an alternative embodiment, the temperature sensor unit 2 is a matrix sensor, i.e., a two-dimensional array of, e.g., 4×4=16 infrared sensors 20 as shown in FIG. 3b.

Due to the scanning of an area, which is made possible hereby, the optimal site (measuring site 6 on the body) for the temperature sensor unit 2, at which the measuring proper of the skin temperature $T_{h1}$ is carried out, can be determined.

An optical system 60 may optionally be associated with the temperature sensor unit 2 in order to amplify the beam path in the direction of the sensor.

The infrared sensor or the infrared sensors of the temperature sensor unit 2 determines/determine the surface temperature $T_{h1}$ of the person, which is closely correlated with the body core temperature. The infrared signals of the temperature sensor unit 2 are converted into electric voltage signals in the downstream display unit 4 and the maximum of the electric voltage is preferably selected for the further calculation. The evaluating unit 3 contains a computer, in which the body core temperature $T_c$ is calculated according to the following formula:

$$T_c = T_{h1} + \frac{\alpha}{K_g} \cdot (T_{h1} - t_{amb}),$$

in which $T_c$=body core temperature to be measured, $T_{h1}$=skin temperature, $t_{amb}$=ambient temperature, $K_g$=coefficient of thermal conduction for the tissue at a defined site, α=heat transfer between the skin and the environment.

The display unit 4 may be connected to the evaluating unit 3 in a wireless manner. For example, the display unit 4 may be arranged integrated in a stationarily arranged evaluating or monitoring station.

To make it possible to guide the infrared sensors of the temperature sensor unit 2 over the measuring area 8 on the body, the scanning unit 5 has an actuator (stepping motor) 58 and/or a joint, so that the temperature sensor unit 2 can be moved along a preset scanning path. The actuator 58 may also be designed as a piezo actuator with a solid joint.

According to an alternative embodiment, shown in FIG. 4, the infrared sensors of the temperature sensor unit 2 may also be arranged stationarily, in which case the optical system 60 arranged in the front is mounted movably via scanner 5 with motor actuator 58. The front-mounted optical system 60 for setting the visual range of the infrared sensors is preferably arranged such that it is integrated in the housing of the temperature sensor unit 2.

The infrared sensors may be designed as thermocouples or as bolometers arranged in a row. The thermocouples or the bolometers may also be arranged in the form of a line.

As can be determined from the above calculation formula, a temperature difference is necessary for determining the body core temperature $T_c$. To make reliable temperature determination always possible, a stabilizing means 70 is provided, which regulates or stabilizes the ambient temperature $T_{amb}$ to a preset temperature. This temperature differs especially from the incubator temperature of the incubator in which the infant 7 is located. The stabilizing means 70 may have, for example, a Peltier cooler. As an alternative, the temperature difference may also be maintained by removing the heat of the infrared sensors through a hole of the incubator hood.

According to an alternative embodiment of the present invention, an orientation field 80, which is placed detachably on the body, may also be associated with the measuring area 8 on the body or the measuring site 6 on the body. The orientation field can be detected by a scanner of the scanning unit 5 and is used as a reference point for the scanning motion of the temperature sensor unit 2. The orientation field may be placed on the body, for example, by means of a color spot that can be resolved. The scanner of the scanning unit 5 may be designed, for example, as a web camera, by means of which the local position of the orientation field can be detected. After determining the orientation field, the temperature sensor unit 2 can now be aligned with the orientation field. The orientation field preferably corresponds to the measuring site 6 on the body, the measuring site 6 on the body being determined automatically by the scanning unit 5. The scanning of the measuring site 6 on the body can subsequently take place in the second step, the temperature sensor unit 5 being adjusted at fixed or variable time intervals in case of movement of the infant 7.

According to an embodiment of the present invention, not shown, a calibration field 90, in which calibration of the temperature measurement can take place, may also be provided at a point of the body or of the thermotherapy apparatus, for example, of an incubator 100. The calibration field is characterized by a defined emissivity and a known temperature.

While specific embodiments of the invention have been shown and described in detail to illustrate the application of the principles of the invention, it will be understood that the invention may be embodied otherwise without departing from such principles.

What is claimed is:

1. A method for the contactless determination of the body core temperature of a person, the method comprising:

detecting the surface temperature of the person at a measuring site on the body by means of a temperature sensor unit arranged at a spaced location therefrom wherein the temperature sensor unit locally identifies a measuring area on the body and the measuring area on the body is scanned by the temperature sensor unit such that a measuring site on the body is determined and the detection of the surface temperature is carried out by said temperature sensor unit at said measuring site on the body;

moving a temperature sensor unit functional sensing point such that said temperature sensor unit functional sensing point is positioned based on a position of said measuring area, whereby said temperature sensor unit is aligned with said measuring area;

sending a sensor signal generated by the temperature sensor unit to an evaluating unit for evaluating the sensor signal and for determining the body core temperature by calculation using the sensor signal generated by the temperature sensor unit; and sending a temperature signal generated in the evaluating unit to a display unit for the optical display of the body core temperature determined.

2. A method in accordance with claim 1, wherein the said measuring site on the body is scanned continuously or at preset time intervals by said temperature sensor unit.

3. A method in accordance with claim 1, wherein said temperature sensor unit is aligned manually or automatically with said measuring area on the body by means of a scanning unit.

4. A method in accordance with claim 1, wherein said measuring area on the body is resolved by means of the temperature sensor unit having a number of infrared sensors or a matrix of infrared sensors.

5. A measuring device for the contactless determination of the body core temperature of a person, the measuring device comprising:
- a temperature sensor defining a measuring area on the body, said temperature sensor unit scanning said measuring area such that said temperature sensor unit determines a measuring site within said measuring area, said temperature sensor unit having a functional sensing point, said temperature sensor unit detecting a surface temperature of the person's body at said temperature measuring site;
- an evaluating unit for evaluating the sensor signal sent by said temperature sensor unit as well as for calculating a temperature signal representing a core temperature of the person's body; and
- a display unit for the visual and/or acoustic display of the body core temperature of the person; and
- a scanning unit associated with said temperature sensor unit for operatively sensing said measuring site such that said functional sensing point follows movement of said measuring site.

6. A measuring device in accordance with claim 5, wherein said scanning unit comprises a one-dimensionally movable and/or two-dimensionally movable sensor carrier, on which said temperature sensor unit is arranged.

7. A measuring device in accordance with claim 5, wherein said temperature sensor unit has at least one infrared sensor as a dot sensor and/or as a row of sensors or a matrix sensor.

8. A measuring device in accordance with claim 5, wherein said scanning unit has an actuator and/or a joint for displacing said temperature sensor unit along a preset scanning path.

9. A measuring device in accordance with claim 5, wherein said temperature sensor unit comprises:
- a bolometer or series-connected thermocouples as a sensor; and
- a stabilizing means for maintaining a temperature difference that is necessary for the measurement between a surface temperature and an ambient temperature.

10. A measuring device in accordance with claim 5, further comprising an orientation field detachably arranged in said measuring area on the body or at said measuring site on the body, so that said orientation field is recognized by means of a scanner of said scanning unit and said temperature sensor unit is aligned with said orientation field.

11. A measuring device in accordance with claim 5, wherein a calibration field of a defined emissivity and/or preset ambient temperature is arranged in said measuring area on the body or at the measuring site on the body or at any desired point of the body, such that the temperature measurement can be calibrated if said temperature sensor unit is aligned with said calibration field.

12. A method for the contactless determination of the body core temperature of a person, the method comprising the steps of:
- providing a temperature sensor unit;
- providing an evaluating unit;
- providing a display unit;
- defining a measuring area on the body via said temperature sensor unit;
- scanning said measuring area with said temperature sensor unit such that said temperature sensor unit determines a temperature measuring site located within said measuring area;
- arranging said temperature sensor unit at a spaced location from said measuring site;
- detecting the surface temperature of the person at said measuring site via said temperature sensor unit;
- operatively sensing said measuring area with said temperature sensor unit such that a functional sensing point of said temperature sensor unit follows movement of said measuring area;
- sending a sensor signal generated by said temperature sensor unit to said evaluating unit, said evaluating unit evaluating said sensor signal, said evaluating unit determining a body core temperature based on said sensor signal generated by said temperature sensor unit; and
- sending a temperature signal generated in said evaluating unit to said display unit, said display unit displaying said body core temperature.

13. A method in accordance with claim 12, wherein said measuring site on the body is scanned continuously or at preset time intervals via said temperature sensor unit.

14. A method in accordance with claim 12, further comprising the step of providing a scanning unit, said scanning unit being connected to said temperature sensor unit, said scanning unit being mounted for movement such that said scanning unit moves said temperature sensor unit.

15. A method in accordance with claim 14, wherein said temperature sensor unit is aligned manually or automatically with said measuring area on the body via said scanning unit.

16. A method in accordance with claim 12, wherein said temperature sensor unit has a plurality of infrared sensors or a matrix of infrared sensors, said infrared sensors determining said measuring area on the body.

* * * * *